(12) United States Patent
Agarkhed et al.

(10) Patent No.: US 10,758,750 B2
(45) Date of Patent: Sep. 1, 2020

(54) CLEANSING COMPOSITION WITH IMPROVED AVAILABILITY OF BENEFIT AGENT

(71) Applicant: Conopco, Inc., Englewood Cliffs, NJ (US)

(72) Inventors: Ajit Manohar Agarkhed, Mumbai (IN); Pravin Bankar, Mumbai (IN); Nitish Kumar, Bihar (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/747,243

(22) PCT Filed: Jul. 4, 2016

(86) PCT No.: PCT/EP2016/065648
§ 371 (c)(1),
(2) Date: Jan. 24, 2018

(87) PCT Pub. No.: WO2017/016803
PCT Pub. Date: Feb. 2, 2017

(65) Prior Publication Data
US 2018/0216046 A1    Aug. 2, 2018

(30) Foreign Application Priority Data

| Jul. 29, 2015 | (IN) | 2875/MUM/2015 |
| Jul. 29, 2015 | (IN) | 2876/MUM/2015 |
| Jul. 29, 2015 | (IN) | 2877/MUM/2015 |
| Oct. 14, 2015 | (EP) | 15189703 |
| Oct. 14, 2015 | (EP) | 15189707 |
| Oct. 14, 2015 | (EP) | 15189709 |

(51) Int. Cl.

| *C11D 3/00* | (2006.01) |
| *A61Q 19/10* | (2006.01) |
| *C11D 3/48* | (2006.01) |
| *A61K 8/36* | (2006.01) |
| *A61K 8/19* | (2006.01) |
| *A61K 8/34* | (2006.01) |
| *A61K 8/86* | (2006.01) |
| *C11D 3/12* | (2006.01) |
| *C11D 3/04* | (2006.01) |
| *C11D 3/20* | (2006.01) |
| *C11D 3/50* | (2006.01) |
| *C11D 10/04* | (2006.01) |
| *C11D 13/16* | (2006.01) |
| *C11D 17/00* | (2006.01) |
| *C11D 9/12* | (2006.01) |
| *C11D 9/26* | (2006.01) |
| *C11D 1/14* | (2006.01) |

(52) U.S. Cl.
CPC ............ *A61Q 19/10* (2013.01); *A61K 8/19* (2013.01); *A61K 8/345* (2013.01); *A61K 8/361* (2013.01); *A61K 8/86* (2013.01); *C11D 3/046* (2013.01); *C11D 3/1206* (2013.01); *C11D 3/2065* (2013.01); *C11D 3/2086* (2013.01); *C11D 3/48* (2013.01); *C11D 3/50* (2013.01); *C11D 9/12* (2013.01); *C11D 9/26* (2013.01); *C11D 10/04* (2013.01); *C11D 10/042* (2013.01); *C11D 13/16* (2013.01); *C11D 17/0047* (2013.01); *C11D 17/0052* (2013.01); *C11D 17/0095* (2013.01); *C11D 1/146* (2013.01)

(58) Field of Classification Search
None
See application file for complete search history.

(56) References Cited

U.S. PATENT DOCUMENTS

| 3,070,547 | A | 12/1962 | Chaffee |
| 4,673,525 | A | 6/1987 | Small et al. |
| 4,988,453 | A | 1/1991 | Chambers et al. |
| 5,041,234 | A | 8/1991 | Instone et al. |
| 5,417,876 | A | 5/1995 | Tokosh et al. |
| 5,496,489 | A | 3/1996 | Dussault et al. |
| 5,703,025 | A | 12/1997 | Zyngier et al. |
| 5,786,311 | A | 7/1998 | Zyngier et al. |
| 6,207,636 | B1 | 3/2001 | Benjamin et al. |
| 6,852,681 | B1 * | 2/2005 | Kerschner .......... C11D 17/0073 510/152 |
| 2001/0031711 | A1 | 10/2001 | Behal et al. |
| 2001/0046950 | A1 | 11/2001 | Agrawal et al. |
| 2003/0027734 | A1 * | 2/2003 | Chokappa ............ C11D 1/04 510/147 |
| 2003/0166480 | A1 | 9/2003 | Sachdev |
| 2005/0277561 | A1 | 12/2005 | Hendrickx et al. |

(Continued)

FOREIGN PATENT DOCUMENTS

| CN | 1157633 | 8/1997 |
| EP | 0434460 | 6/1991 |

(Continued)

OTHER PUBLICATIONS

Search Report & Written Opinion in PCTEP2016065641, dated Aug. 30, 2016.
Search Report & Written Opinion in PCTEP2016065648, dated Aug. 30, 2016.
Search Report and Written Opinion in EP17189707, dated Mar. 30, 2016.

(Continued)

*Primary Examiner* — Necholus Ogden, Jr.
(74) *Attorney, Agent, or Firm* — Edward A. Squillante, Jr.

(57) ABSTRACT

The present invention provides a cleansing composition comprising 10 to 30 wt % soap, 20 to 45 wt % water soluble organic solvent, 20 to 40 wt % water, 3 to 20 wt % electrolyte other than soap and a benefit agent.

18 Claims, No Drawings

(56) References Cited

U.S. PATENT DOCUMENTS

| | | | |
|---|---|---|---|
| 2011/0077186 A1* | 3/2011 | Lai | C11D 9/225 510/141 |
| 2011/0143984 A1 | 6/2011 | Yang et al. | |
| 2013/0130960 A1 | 5/2013 | Astolfi et al. | |
| 2014/0024573 A1 | 1/2014 | Agarkhed et al. | |
| 2014/0053508 A1 | 2/2014 | Chourey et al. | |
| 2014/0343155 A1 | 11/2014 | Jayaraman et al. | |
| 2015/0030557 A1 | 1/2015 | Gizaw et al. | |
| 2016/0053207 A1* | 2/2016 | Chandar | C11D 3/48 422/28 |

FOREIGN PATENT DOCUMENTS

| | | |
|---|---|---|
| EP | 0552024 | 7/1993 |
| EP | 2154234 | 2/2010 |
| GB | 850355 | 10/1960 |
| GB | 2186883 | 8/1987 |
| GB | 200516897 | 9/2005 |
| IN | 177828 | 2/1997 |
| IN | 01021MU2004 | 6/2007 |
| IN | 282588 | 4/2017 |
| KR | 100701111 | 3/2007 |
| PH | 2010000295 | 1/2013 |
| TW | 340871 | 9/1998 |
| TW | 341598 | 10/1998 |
| WO | WO9604360 | 2/1996 |
| WO | WO03010272 | 2/2003 |
| WO | WO2005068594 | 7/2005 |
| WO | WO03010273 | 2/2006 |
| WO | WO06094586 | 9/2006 |
| WO | WO08055765 | 5/2008 |
| WO | WO08071561 | 6/2008 |
| WO | WO08149951 | 12/2008 |
| WO | WO2010089269 | 8/2010 |
| WO | WO2011080101 | 7/2011 |
| WO | WO2012136502 | 10/2012 |
| WO | WO2013143808 | 10/2013 |
| WO | WO2014170186 | 10/2014 |
| ZA | 9700280 | 7/1998 |

OTHER PUBLICATIONS

Search Report and Written Opinion in PCTEP2016065676, dated Aug. 30, 2016.
Copending Application for Agarkhed et al.; U.S. Appl. No. 15/747/230; dated Jan. 24, 2018.
Copending Application for Agarkhed et al.; U.S. Appl. No. 15/747/234; dated Jan. 24, 2018.

* cited by examiner

CLEANSING COMPOSITION WITH IMPROVED AVAILABILITY OF BENEFIT AGENT

FIELD OF THE INVENTION

The present invention relates to cleansing compositions, particularly to rinse-off cleansing compositions such as cleansing bars, which include one or more benefit agents with improved availability at the time of intended use.

BACKGROUND OF THE INVENTION

Difficulties frequently arise in achieving effective deposition of benefit agents onto hair or skin when the benefit agent is delivered by means of incorporation into rinse-off compositions, typically hair and body shampoos. Especially benefit agents which are water- and/or surfactant-soluble are often preferentially rinsed away from the intended site of deposition, rather than being deposited thereat and there have hitherto been numerous proposals in the art seeking to enhance deposition of such materials from these kinds of compositions.

This problem is particularly pronounced in the context of cleansing compositions, where the benefit agent to be deposited is surfactant-soluble, yet may still be water-insoluble. Hitherto there has been little, even no, study of deposition problems of specifically surfactant-soluble, often oily, benefit agents from this type of system.

There is much prior art relating to oil-based cleansing compositions such as in the form of creams, lotions, gels, milks or the like, e.g. comprising emulsions, which contain oily benefit agents such as sunscreens for deposition onto skin. As well as being intended primarily as a leave-on, rub-off-resistant and often water-resistant type of product, these compositions also contain no or little surfactant, so are unsuitable for cleansing purposes, either for the skin or for the hair.

Modification of these known compositions by simple addition of surfactant in order to give desirable detergency properties is not possible, because little deposition of the sunscreen or other benefit agent which is surfactant-soluble results, as a consequence of the agent being solubilized by the surfactant and easily carried away from the intended site of deposition as the composition is rinsed off.

US2015030557 (PROCTER AND GAMBLE CO) discloses consumer product compositions providing enhanced hydrophobic benefit agent deposition. The benefit agent is provided as a benefit agent/deposition aid emulsion, where the benefit agent is physically adsorbed to the deposition aid before the emulsion is added to the balance of ingredients. The emulsions and products facilitate increased deposition and retention of benefit agents contained therein onto a substrate.

WO/2005/068594 (UNILEVER PLC) discloses a cleansing composition capable of enhancing deposition of benefit agent comprising: i. a functional oil-in-water emulsion comprising 0.1% to 5% by weight benefit agent solubilised/dispersed in an oil and emulsified in water using a cationic emulsifier having an HLB greater than 8 such that the ratio of oil:cationic emulsifier is in the range 20:1 to 1:1; ii. a detergent active composition comprising 5% to 80% detergent active; and iii. a cationic polymer.

EP0552024 (Unilever) discloses rinse-off cleansing composition including one or more surfactant-soluble cosmetic agents for deposition onto hair or skin, the composition comprising a stable emulsion having a continuous phase comprising one or more surfactants and an internal phase comprising one or more oil materials, wherein the internal oil phase contains the said one or more surfactant-soluble cosmetic agents.

There therefore exists in the art a problem of poor availability and deposition of surfactant-soluble benefit agent from a rinse-off cleansing composition containing significant amounts of surfactant. Among other disadvantages, this leads to non-cost-effective use of and waste of (which may possibly be undesirable for environmental or health reasons) cleansing raw materials.

SUMMARY OF THE INVENTION

The present invention provides a cleansing composition capable of improving the availability and enhancing deposition of benefit agent.

One aspect of the present invention provides a cleansing composition comprising: 10 to 30 wt % soap, 20 to 45 wt % water soluble organic solvent, 20 to 40 wt % water, 3 to 20 wt % electrolyte other than soap, and a benefit agent.

These and other aspects features and advantages will become apparent to those of ordinary skill in the art from a reading of the following detailed description and the appended claims.

DETAILED DESCRIPTION OF THE INVENTION

For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about".

Numerical ranges expressed in the format "from x to y" are understood to include x and y. When for a specific feature multiple preferred ranges are described in the format "from x to y", it is understood that all ranges combining the different endpoints are also contemplated.

The present invention relates to a shaped solid cleaning composition. By the term "cleansing composition" is meant a composition which is used to clean any substrate e.g. skin, hair or other external surfaces of human or animal body, or hard surfaces in homes, offices or any public or industrial location or soft/porous substrates like fabric. By "shaped solid" is meant a body in solid form which retains its shape after manufacture and during transport and storage. Examples of shaped solids include bars and tablets.

As used herein % or wt % refers to percent by weight of an ingredient as compared to the total weight of the composition or component that is being discussed.

Cleansing bars produced from compositions according to the invention in addition to being capable of being processed at high production rates also possess a range of desirable physical properties that make them highly suitable for everyday use by mass market consumers.

The present invention relates to cleansing compositions, particularly to rinse-off cleansing compositions, which include one or more benefit agents to be deposited onto a surface. The invention is especially concerned with improving the availability of benefit agents from such compositions, compared with that from similar compositions of this type found in the prior art.

The present invention provides a cleansing composition comprising: 10 to 30 wt % soap, 20 to 45 wt % water soluble organic solvent, 20 to 40 wt % water, 3 to 20 wt % electrolyte other than soap, and a benefit agent.

Surprisingly, the inventors of the present invention have found that it is possible to improving availability of surfactant-soluble benefit agents from rinse-off cleansing compositions, by use of the present composition.

It was an unexpected finding of the present invention that the low soap content of the composition, lead to enhanced availability of the benefit agent.

Benefit Agent—

A wide variety of one or more benefit agents can be comprised in the composition of the present invention, such as a fragrance, an antimicrobial agent, a biocontrol agent, a sunscreen agent, a moisturizing agent, an emollient, or a combination thereof. These benefit agents are known in the art.

It is preferred that the benefit agent of the present invention is surfactant soluble. It is also preferred that the benefit agent of the present invention is hydrophobic.

Preferred benefit agents are listed below, but their list is not comprehensive.

The Preferred benefit agents are moisturizers, emollients, sunscreens, fragrances, cosmetic ingredients, antimicrobial agent and anti-ageing compounds. The agents may be added at an appropriate step during the process of making the composition.

Examples of moisturizers and humectants include cetyl alcohol, CARBOPOL® 934, ethoxylated castor oil, paraffin oils, lanolin and its derivatives. Silicone compounds such as silicone surfactants like DC® 3225C (Dow Corning) and/or silicone emollients, silicone oil (DC-200® ex. Dow Corning) may also be included. Sunscreens such as 4-tertiary butyl-4'-methoxy dibenzoylmethane (available under the trade name PARSOL® 1789 from Givaudan) or 2-ethyl hexyl methoxy cinnamate (available under the trade name PARSOL® MCX from Givaudan) or other UV-A and UV-B sun-screens may also be added. Lipids such as cholesterol, ceramides, and pseudoceramides, and exfoliant particles such as polyethylene beads, walnut shells, apricot seeds, flower petals and seeds may also be present. Structurants such as maltodextrin or starch may be used to structure the bars. Preferred bars may also include essential oils such as bergamot and citrus or insoluble extracts of avocado, grape, grapeseed, myrrh, cucumber, watercress, calendula, elder flower, geranium, linden blossom, amaranth, seaweed, gingko, ginseng and other plant extracts.

Examples of useful sunscreen agents are octyl methoxyl cinnamate (Parsol MCX) and butyl methoxy benzoylmethane (Parsol 1789). Other examples of useful sunscreen agents are disclosed in the published patent application WO 03/075879 on page 4, lines 15-31 and on page 5, the teaching of which is incorporated herein by reference.

Other preferred benefit agents include:
a) silicone oils, gums and modifications thereof such as linear and cyclic olydimethylsiloxanes, amino, alkyl alkylaryl and aryl silicone oils;
b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenatmg the aforementioned oils; and synthetic mono, di and triglycerides such as myristic acid glyceride and 2-ethylhexanoic acid glyceride;
c) waxes such as carnauba, spermaceti, beeswax, lanolin and derivatives thereof;
d) hydropnoDic plant extracts;
e) hydrocaroons such as liquid paraffins, petroleum jelly, microcrystalline wax, ceresin, squalene, squalane, and mineral oil;
f) higher fatty acids such as lauric, myristic, palmitic, stearic, behenic, oleic, linoleic linolenic, lanolic, isostearic and poly unsaturated fatty acids (PUFA) acids;
g) higher alcohols such as lauryl, cetyl, steryl, oleyl, behenyl, cholesterol and 2-hexadecanol alcohol;
h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;
i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;
j) lipids such as cholesterol, ceramides, sucrose esters and pseudo-ceramides as described in European Patent Specification No. 556 957;
k) vitamins such as vitamin A and E, and vitamin alkyl esters, including chose vitamin C alkyl esters;
l) sunscreens such as octyl methoxyl cmnamate (Parsol MCX) and butyl methoxy benzoyimetnane (Parsol 1789)
m) Phospnolipids; and
n) mixtures of any of the foregoing components.

Where adverse interactions between the benefit agent and soap or non-soap surfactant are likely to be particularly acute, the benefit agent may be incorporated in the compositions of the invention in a carrier.

Such benefit agents include lipids; alkyl lactates; sunscreens; esters such as isopropyl palmitate and isopropyl myristate; and vitamins. The carrier can, for example, be a silicone or hydrocarbon oil which is not solubilised/micellised by the surface active phase and in which the benefit agent is relatively soluble.

Particularly preferred benefit agents include those that are water-insoluble and more preferably those having log P values in the range of 0.4 to 12, more preferably 0.8 to 8.5 and most preferably in the range of 1 to 6.5.

Particularly preferred benefit agents include silicone oils, fragrance, polymers and modification thereof; esters such as isopropyl palmitate and myristate and alkyl lactates.

The benefit agent can be provided in the form of an emulsion.

It is preferred that the benefit agent of the present invention is present in the range of 0.00005 to 5%, more preferably in the range of 0.001 to 3% and most preferably 0.1 to 2.5% by weight of the composition.

Fragrance

A particularly preferred benefit agent is fragrance.

The term "fragrance" is defined as a mixture of odoriferous components, optionally mixed with a suitable solvent diluent or carrier, which is employed to impart a desired odor.

Fragrance components and mixtures thereof may be obtained from natural products such as essential oils, absolutes, resinoids, resins and concretes, as well as synthetic products such as hydrocarbons, alcohols, aldehydes, ketones, ethers, carboxylic acids, esters, acetals, ketals, nitriles and the like, including saturated and unsaturated compounds, aliphatic, carbocyclic and heterocyclic compounds.

By fragrance is meant any volatile perfume agent which provides an aroma to the final composition in which the fragrance resides. Examples of such materials are those boiling at temperatures below about 500° C. The highly volatile, low boiling, perfume ingredients typically have boiling points of about 250° C. or lower. The moderately volatile perfume ingredients are those having boiling points of from about 250° C. to about 300° C. The less volatile, high boiling, perfume ingredients are those having boiling points of about 300° C. to about 500° C. Many of the perfume ingredients as discussed hereinafter along with their odor and/or flavor characters, and their physical and chemical properties, such as boiling point and molecular weights are given in "Perfume and Flavor Chemicals (Aroma Chemicals)," Steffen Arctander, published by the author, 1969, incorporated herein by reference. It is preferred that the personal cleansing compositions herein contain a fragrance having at least about 5% of its components, more preferably at least about 25%, and most preferably at least about 50% of the fragrance components as highly volatile perfume ingredients having a boiling point of 250° C. or lower.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol. geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene. beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Fragrance further include spices or flavor enhancers which contribute to the overall flavor perception of the composition, such as perfumes or perfume raw materials. A disclosure of suitable perfume raw materials, traditionally used in perfumery, can be found in "Perfume and Flavor Chemicals", Vol. I and II, S. Arctander, Allured Publishing, 1994, ISBN 0-931710-35-5. Examples of fragrance include essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, thymol, spirantol, penene, limonene and terpenoid oils.

Suitable characteristics of fragrances can include at least one of the following, in any combination: (1) liquid or semi-liquid after mixing with the other components; (2) pleasant and/or clean odor when mixed with other components, e.g., one or more of lavender, violet, rose, jasmine, pine, woody, floral, fruity, lemon, lime, apple, peach, raspberry, strawberry, banana, plum, apricot, vanilla, pear, eucalyptus, aromatic, aldehydic, tutti frutti, oriental, sweet, amber, Paola, Muguet, Citron (lime) ella, and the like; (3) specific gravity (20/20) in the range of 0.600-1.300, preferably 0.800-1.100, each preferably varying 0.001-0.05, more preferably 0.008-0.020; (4) refractive index (20° C.) of 1.300-1.800, preferably 1.400-1.600, each preferably varying 0.001-0.05, more preferably 0.008-0.020; (5) saponification value of 5-300, preferably 10-250; and (6) having a flash point of 20-200 Pensky-Martens Closed Cup (P.M.C.C.) and 10-100 Tag-Closed Cup (T.C.C).

Typical fragrance components which may be employed for the present invention can be selected from one or more of: 2-methoxy naphthalene, Allyl cyclohexane propionate, alpha-citronellal, alpha-ionone, alpha-Santalol, alpha-Terpineol, Ambrettolide, Amyl benzoate, Amyl cinnamate, Amyl cinnamic aldehyde, Aurantiol, Benzaldehyde, Benzophenone, Benzyl acetate, Benzyl salicylate, Beta-caryophyllene, beta-Methyl naphthyl ketone, Cadinene, Cavacrol, Cedrol, Cedryl acetate, Cedryl formate, Cinnamyl cinnamate, cis-Jasmone, Coumarin, Cyclamen aldehyde, Cyclohexyl salicylate, d-Limonene, delta-Nonalactone, delta-Undecalactone, Dihydro isojasmonate, Dimethyl acetal, Diphenyl methane, Diphenyl oxide, Dodecalactone, Ethyl methyl phenyl glycidate, Ethyl undecylenate, Ethylene brassylate, Eugenol, Exaltolide, Galaxolide, gamma-n-methyl ionone, gamma-Undecalactone, Geranial, Geranyl acetate, Geranyl anthranilate, Geranyl phenyl acetate, Hexadecanolide, Hexenyl salicylate, Hexyl cinnamic aldehyde, Hexyl salicylate, Hydroxycitronellal, Indole, Iso E super, Iso-Amyl salicylate, Iso-bornyl acetate, Iso-butyl quinolone, Iso-Eugenol, Laevo-Carvone, Lilial (p-t-bucinal), Linalool, Linalyl acetate, Linalyl benzoate, Methyl cinnamate, Methyl dihydrojasmonate, Methyl-N-methyl anthranilate, Musk indanone, Musk ketone, Musk tibetine, Myristicin, Nerol, Oxahexadecanolide-10, Oxahexadecanolide-11, para-cymene, para-tert-Butyl cyclohexyl acetate, Patchouli alcohol, Phantolide, Phenyl ethyl alcohol, Phenyl ethyl benzoate, Phenyl heptanol, Phenylhexanol, Phexylethylphenylacetate, Thibetolide, Vanillin, Vertenex, Vetiveryl acetate, Yara-yara and Ylangene.

Still additional fragrance components (used either alone or in combination) suitable for use in this invention include those often characterized as low volatile fragrances. Such fragrances include but are not limited to: Camphor, 5-methyl, 2-1-cyclohexanone, Allyl heptanoate, Allyl-terpineol, Gardenol, Citronellol, Phenylethyl acetate, Citral, Alpha-terpinolene, 2-tertiobytycyclo hexyl, Tertbutyl cyclohexyl acetate, Beta-ionone, 4-tert-butylcyclohexyl acetate, Alpha-terpinene, 2,6-dimethyl ocatadiene, Damascone, Benzene, 1,1, oxybis, Beta methylionone, Octalactone, Ethyl ester decadienoic, Methyl ionone, Rose phenome, Dihydro methyl jasmonate, Ambrox, Benzyl benzoate, Iso-amyl acetate, Ethyl methyl valerate, 2-octanone, Hexyl acetate, Iso-amyl acetate, Limonene, Butyl isovalerate, Dihydromyrcenol, Tripal, Terpinolene, Tripal 2, Cyclohexano, 2,1,1 methyl ethyl, Orange crystals, Peach lactone, Citronellyl acetate and Alpha terpinyl acetate.

Suitable solvents, diluents or carriers for perfumes as mentioned above are for example: ethanol, isopropanol, diethylene glycol monoethyl ether, dipropyl glycol, triethyl citrate and the like.

Particularly preferred fragrance components of the present invention are cyclic and acyclic terpenes and terpenoids. These materials are based upon isoprene repeating units.

Examples include alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof.

Amounts of the fragrance may range from 0.00005 to 5%, more preferably in the range of 0.001 to 3% and most preferably 0.1 to 2.5% based on the weight of the cleansing composition.

The cleansing compositions of the present invention may be in any form. These forms may include lotions, creams, roll-on formulations, sticks, mousses, aerosol and non-aerosol sprays and fabric (e.g. nonwoven textile)-applied formulations. It is preferable that the cleansing compositions of the present invention are solid and most preferably in the form of a cleansing bar.

Fragrance benefits, used in this specification, can include improved availability, enhanced deposition on skin, extended release of fragrance from the skin, selective deposition on skin of specific compounds associated with providing an aroma, and the like. The fragrance should be present in quantities to provide an aroma. It is preferred that the fragrance of the present invention is present in the range of 0.00005 to 5%, more preferably in the range of 0.001 to 3% and most preferably 0.1 to 2.5% by weight of the composition. A maximum quantity is generally dependent upon the strength and quantity of aroma desired.

Hydrophobicity and Log P Value

Hydrophobicity is the physical property of a molecule (known as a hydrophobe) that is seemingly repelled from a mass of water.

A pure substance may distribute itself between two miscible solvents such as a hydrocarbon component & water. This partition coefficient is definite equilibrium physico-chemical property of a pure substance under specified conditions. It is function of the Gibbs energy of transfer from water to octanol hence describes the thermodynamic tendency of the compound to partition in different media.

Generally 1-octanol & water is the chosen to co-relate partion coefficient. The octanol-water partition coefficient of a substance X at a given temperature is represented by "P" and defined by superscripts "org" & "aq" used to denote mutually saturated phases & "oct" & 'W" for pure solvents.

$$P=[X]^{org}/[X]^{aq},$$

i.e the ratio of concentrations (mole/volume) at equilibrium: it is therefore unitless. Further, P is defined is as the quantity which is independent of concentration i.e. that value for which the solute obeys Henrys law in both solvents simultaneously. In practice P is determined at high dilution or extrapolated to zero concentration. Since P is measured over many magnitudes it is usually expressed as its decadic logarithm, log P.

Log P is the n-octanol/water partition coefficient that can be used to relate chemical structure to observed chemical behavior. Log P is related to the hydrophobic character of the molecule. The Log P values were calculated within Cerius2, using 25 QSAR+, which is a program obtained from Accelrys Inc., 9685 Scranton Road, San Diego, Calif. 92121. The QSAR+descriptor A Log P and molar refractivity are calculated using the method described by Ghose Crippen (1989). In this atom-based approach, each atom of the molecule is assigned to a 30 particular class, with additive contributions to the total value of log P and molar refractivity. For more information about this descriptor the reader is directed to Leffler and Grunwald (1963).

It is preferred that the hydrophobic compounds that are used as benefit agents in the present invention have a log P value ranging from 0.4 to 12, more preferably 0.8 to 8.5 and most preferably from 1.5 to 6.5. A non-comprehensive but exemplary list of such compounds is provided in the table below:

TABLE 1

| S. No. | Compound | Log P Value |
|---|---|---|
| 1. | Limonene | 4.58 |
| 2. | Caryophylene | 5.35 |
| 3. | beta pinene | 0.94 |
| 4. | 1,8 cineole (eucalyptol) | 2.74 |
| 5. | p-cymene | 3.73 |
| 6. | Isobornyl acetate | 3.6 |
| 7. | Linalool | 2.97 |
| 8. | Terpineol | 2.69 |
| 9. | Camphor | 2.38 |
| 10. | Camphene | 4.56 |
| 11. | Alpha pinene | 4.83 |
| 12. | Terpinen-4-ol | 1.06 |
| 13. | Verbenone | 1.97 |
| 14. | Fenchone | 2.13 |
| 15. | Carvone | 2.23 |
| 16. | Terpineol | 2.67 |
| 17. | Perillyl alcohol | 3.07 |
| 18. | Limonene | 4.58 |
| 19. | Nerolidol | 5.36 |
| 20. | Farnesol | 5.31 |
| 21. | Linalool | 3.28 |
| 22. | Geraniol | 3.18 |
| 23. | Menthol | 3.2 |
| 24. | 4-chloro-3,5-dimethylphenol- | 2.93 |
| 25. | Thymol- | 3.09 |
| 26. | 4-chloro-3,5-dimethylphenol- | 2.93 |

Total Fatty Matter

The term total fatty matter is used very widely and popularly in the field of soaps and detergents. The term Total Fatty Matter, abbreviated to "TFM", is used to denote the soap obtained from fatty acids and triglycerides present in the cleansing composition without taking into account the accompanying cations. For a soap having 18 carbon atoms, an accompanying sodium cation will generally amount to about 8 percent by weight of a mole of soap. Other cations may be employed as desired, for example zinc, potassium, magnesium, alkyl ammonium and aluminium. To calculate the "soap" level in the personal wash composition, the TFM level is to be multiplied by 1.08.

The TFM content of disclosed composition is at most 35 wt %, more preferably between 15 to 35 wt %, and most preferably 20 to 30% based on weight of the composition.

Soaps of Fatty Acids

The term soap means salts of fatty acids. Preferably, the soap is soap of $C_8$ to $C_{24}$ fatty acids, more preferably of $C_{10}$ to $C_{18}$ fatty acids. It is particularly preferred that the soap includes at least 40 wt % soaps of $C_8$ to $C_{14}$ fatty acids, more preferably at least 50 wt % and most preferably at least 70 wt % of the total soap content. It is also preferred that the cleansing composition of the present invention includes at most 60 wt % of the soaps of $C_{16}$ to $C_{22}$ fatty acids, preferably at most 50 wt % and most preferably at most 30 wt % of the total soap content. It is preferred that 30% to 60% of the total soap content is insoluble soap and 40 to 70% of the total soap content is soluble soap.

The cation may be an alkali metal, alkaline earth metal or ammonium ion, preferably alkali metals. Preferably, the cation is selected from sodium or potassium. The soap may be saturated or unsaturated. Saturated soaps are preferred over unsaturated soaps for stability. The oil or fatty acids may be of vegetable or animal origin.

The soap may be obtained by saponification of oils, fats or fatty acids. The fats or oils generally used to make soap bars may be selected from tallow, tallow stearins, palm oil, palm stearins, soya bean oil, fish oil, castor oil, rice bran oil, sunflower oil, coconut oil, babassu oil, and palm kernel oil. The fatty acids may be from coconut, rice bran, groundnut, tallow, palm, palm kernel, cotton seed or soyabean.

The fatty acid soaps may also be synthetically prepared (e.g. by the oxidation of petroleum or by the hydrogenation of carbon monoxide by the Fischer-Tropsch process). Resin acids, such as those present in tall oil, may also be used. Naphthenic acids may also be used.

The term water-soluble soap wherever used in this description means soap having solubility greater than 2 g/100 g water at 25° C.

Insoluble and Soluble Soaps

Soap bars consist of mixture of soaps with different chain lengths and chain saturations. They are classified as soluble soaps and insoluble soaps. The soluble soaps usually form a hexagonal liquid crystalline phase with water which dissolves in water during washing and provides lather. The insoluble soaps stay in crystalline formats in the bar and provide mechanical strength. The solid crystals present in the soap bar can include kappa, zeta, eta and delta phases. The amount of soluble and insoluble phase in the soap bar is strongly dependent on the water content and the amount of sheer/working the soap bar has been subjected to at temperatures above or below the Krafft point of the soap molecules. Increasing water content results in an increase in the amount of soluble soap and consequently a reduction in soap hardness. Addition of small quantities of electrolyte and perfume can also influence the liquid and solid ratio. Electrolyte reduces the soap solubility and therefore increasing the solid phase amount while perfume increases the soluble soap amount. (*Kirk-Othmer Chemical Technology of Cleansings*, 2012).

Soap Phases

It is generally known that soap (cleansing products) exists as a mixture of solid, liquid crystal & isotropic liquid phases. Characterization of these phases is made using low angle X ray diffraction or NMR. Solid phase is further characterized by size.

For the purpose of present invention, the solid phase includes the solid crystals and the liquid phase includes the liquid and the liquid crystal phase.

Liquid crystal phase is formed due to aggregation of micelles & their arrangement pattern, namely—lamellar, hexagonal, these are characterized by NMR due to differential relaxation times (*Hand book of detergents Part-E-Uri Zoeller*).

In conventional extruded soap, a mixture of two separate crystal types forms at thermodynamic equilibrium. One crystal type, referred to as delta phase, is composed of the less soluble saturated long-chain soaps (e.g., C16 and C18 soaps) and is dispersed in a continuum of another crystal type composed of the more soluble saturated short-chain soaps and unsaturated soaps (e.g., C12 and C18:1 soaps), referred to as eta phase. The configuration of less soluble soaps dispersed in a continuum of more soluble soaps can be compared to "bricks and mortar" structure. The continuous phase (the "mortar"), which is composed of the more soluble soaps, will also contain more water than the dispersed phase (the "bricks"), which is composed of the less soluble soaps. Further, because solid soap and water have different refractive indices (n=1.5 for solid soap, n=1.0 for water), these two phases will have different refractive indices. Thus, incident light can be scattered as it passes through the different phases in the cleansing composition. Large dispersed soap crystals, entrapped air, and surface roughness will also scatter light, and dark objects present in the cleansing composition will absorb light.

For the purpose of the present invention, "insoluble soap" refer to monovalent salts of saturated fatty monocarboxylic acids having a carbon chain length of 16 to 24, preferably 18 to 22. "Soluble" soap on the other hand refers to monovalent salts of saturated fatty monocarboxylic acids having a carbon chain length of 8 to 14 and monovalent salts of oleic acid and polyunsaturated fatty monocarboxylic acids having a carbon chain length of 8 to 24.

It is particularly preferred that the soap includes at least 40 wt % soaps of $C_8$ to $C_{14}$ fatty acids, more preferably at least 50 wt % and most preferably at least 70 wt % of the total soap content. It is also preferred that the cleansing composition of the present invention includes at most 60 wt % of the soaps of 016 to 022 fatty acids, preferably at most 50 wt % and most preferably at most 30 wt % of the total soap content.

Non-Soap Surfactant

In addition to the soap of fatty acids, preferred bars may include a non-soap surfactant, which acts as a co-surfactant and which is selected from anionic, non-ionic, zwitterionic, amphoteric and cationic surfactants. Preferred bars include 0.0001 to 15 wt % non soap-surfactants based on the weight of the composition. More preferred bars include 2 to 10 wt % co-surfactant and most preferred compositions include 2.5 to 6 wt % co-surfactant based on the weight of the composition.

Suitable anionic surfactants include water soluble salts of organic sulphuric reaction products having in the molecular structure an alkyl radical containing from 8 to 22 carbon atoms, and a radical chosen from sulphonic acid or sulphuric acid ester radicals, and mixtures thereof.

Examples of suitable anionic surfactants are sodium and potassium alcohol sulphates, especially those obtained by sulphating the higher alcohols produced by reducing the glycerides of tallow or coconut oil; sodium and potassium alkyl benzene sulphonates such as those in which the alkyl group contains from 9 to 15 carbon atoms; sodium alkyl glyceryl ether sulphates, especially those ethers of the higher alcohols derived from tallow and coconut oil; sodium coconut oil fatty acid monoglyceride sulphates; sodium and potassium salts of sulphuric acid esters of the reaction product of one mole of a higher fatty alcohol and from 1 to 6 moles of ethylene oxide; sodium and potassium salts of alkyl phenol ethylene oxide ether sulphate with from 1 to 8 units of ethylene oxide molecule and in which the alkyl radicals contain from 4 to 14 carbon atoms; the reaction product of fatty acids esterified with isethionic acid and neutralized with sodium hydroxide where, for example, the fatty acids are derived from coconut oil and mixtures thereof.

The preferred water-soluble synthetic anionic surfactants are the alkali metal (such as sodium and potassium) and alkaline earth metal (such as calcium and magnesium) salts of higher alkyl benzene sulphonates and mixtures with olefin sulphonates and higher alkyl sulphates, and the higher fatty acid monoglyceride sulphates.

Suitable nonionic surfactants can be broadly described as compounds produced by the condensation of alkylene oxide groups, which are hydrophilic in nature, with an organic hydrophobic compound which may be aliphatic or alkyl aromatic in nature.

The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensate containing from 40 to 80 percent of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide; fatty acid alkylolamides; alkylene oxide condensates of fatty acid alkylolamides and alkyl mercaptans.

Suitable cationic surfactants that can be incorporated are alkyl substituted quarternary ammonium halide salts e.g. bis (hydrogenated tallow) dimethylammonium chlorides, cetyltrimethyl ammonium bromide, benzalkonium chlorides and dodecylmethylpolyoxyethylene ammonium chloride and amine and imidazoline salts for e.g. primary, secondary and tertiary amine hydrochlorides and imidazoline hydrochlorides.

Suitable amphoteric surfactants are derivatives of aliphatic secondary and tertiary amines containing an alkyl group of 8 to 18 carbon atoms and an aliphatic radical substituted by an anionic water-solubilising group, for instance sodium 3-dodecylamino-propionate, sodium 3-dodecylaminopropane sulphonate and sodium N-2-hydroxydodecyl-N-methyltaurate.

Suitable zwitterionic surfactants are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N—N-dimethyl-N-hexadecylammonium) propane-1-sulphonate betaine, 3-(dodecylmethyl sulphonium) propane-1-sulphonate betaine and 3-(cetylmethylphosphonium) ethane sulphonate betaine.

Further examples of suitable detergent-active compounds are compounds commonly used as surface-active agents given in the well-known textbooks "Surface Active Agents", Volume I by Schwartz and Perry and "Surface Active Agents and Detergents", Volume II by Schwartz, Perry and Berch.

Water Soluble Organic Solvent

The water soluble organic solvent is preferably selected from the group consisting of polyol, hydrotropes and mixtures thereof and most preferably polyol. The water soluble organic solvent is preferably in the range of 20 to 45 wt %, more preferably in the range of 25% to 40 wt %, and most preferably in the range of 30 to 40 wt % based on the weight of the composition.

The preferred water soluble organic solvent of the cleansing composition of the present invention include 20% to 45 wt % polyols based on the weight of the composition. Preferred polyols include one or more of glycerol, sorbitol, propylene glycol or polyethylene glycol. Usually a mixture is used. More preferred cleansing composition includes 25 to 40 wt % polyols and most preferred compositions include 30 to 40 wt % of polyols. Polyhydric alcohols (polyols), such as propylene glycol, may serve as diluents to thin out the otherwise thick mixture of caustic soda and fatty acids.

Other polyols such as glycerol perform as a humectant and moisturizer. A mixture of polyols is usually used. When included, polyethylene glycol used in the invention preferably has a molecular weight of from 200 to 1500 Da.

When sorbitol is included, it is preferably present in 5 to 40 percent, more preferably 8 to 25 percent by weight of the composition. When glycerol is included, it is preferably present in 0.5 to 40 percent, more preferably 0.5 to 25 percent by weight of the composition. When polyethylene glycol is included, it is preferably present in 1 to 15 percent more preferably 2 to 10 percent by weight of the composition. When propylene glycol is included, it is preferably present in 0.1 to 15 percent, more preferably 2 to 10 percent by weight of the composition. It is preferred that the composition includes a mixture of sorbitol, polyethylene glycol and propylene glycol. It is most preferred to further include glycerol in addition to the above listed three polyhydric alcohols.

Polyhydric alcohols suitable for use according to the invention include poly (ethylene glycol), propylene glycol, glycerol and sorbitol, i.e., they include dihydric alcohols and polymers with hydroxyl groups. Especially preferred is a mixture of glycerin and sorbitol. The polyhydric alcohol is suitably added a) before saponification or b) before and after saponification.

Hydrotopes include but are not limited to sodium cumene sulphonate, sodium toluene sulphonate, sodium xylene sulphonate & sodium alkyl aryl sulfonate, their derivatives and combinations thereof.

Electrolyte

Optimum electrolyte content is important for the cleansing compositions of the present invention, especially when the compositions are in solid form such as a soap bar. This is because the electrolyte content influences a variety of soap parameters. Addition of small quantities of electrolyte influences the liquid and solid phase ratio. Increasing the electrolyte reduces the soap solubility and therefore increasing the solid phase amount, on the other hand lowering electrolyte levels will make the cleansing bar soft.

The electrolyte contents of the present invention is preferred in the range of 3 to 20 wt %, more, preferably in the range of 3.5 to 15 wt % and most preferably in range of 4 to 10 wt % by weight of the composition. Preferred electrolytes of the present invention include sodium sulfate, sodium chloride, sodium acetate, sodium citrate, potassium chloride, potassium sulfate, sodium carbonate and other mono, di or tri salts of alkaline earth metals, more preferred electrolytes are sodium chloride, sodium sulfate, sodium citrate, potassium chloride and especially preferred electrolytes are sodium chloride, sodium sulfate, and sodium citrate and combinations thereof. For the avoidance of doubt is clarified that the electrolyte is a non-soap material.

It is highly preferred that the electrolyte contents of the present invention is in the range of 4 to 20%, more preferably 5 to 19% and most preferably 6 to 18% by weight of the composition.

Alcohol

The cleansing composition may preferably include 0.05 to 5 wt % alcohol, more preferably from 0.1 to 4 wt % and most preferably from 0.9 to 3 wt % based on the weight of the composition. These include ethanol and isopropyl alcohol. Isopropyl alcohol is more preferred.

Opacifier

An opacifier may be optionally present in the composition. When opacifiers are present, the cleansing composition is generally opaque, i.e. "opacification". Examples of opacifiers include titanium dioxide, zinc oxide and the like. A particularly preferred opacifier that can be employed when an opaque rather than a transparent soap composition is desired is ethylene glycol mono- or di-stearate, for example in the form of a 20% solution in sodium lauryl ether sulphate. An alternative opacifying agent is zinc stearate Transparency is compromised when light passing though is scattered, this can happen if due larger soap crystals.

The product can take the form of a water-clear, i.e. transparent, liquid soap, in which case it will not contain an opacifier, or alternatively, it can take the form of an opaque liquid soap containing an opacifier such as that herein defined.

Water

Preferred cleansing bar includes 20 to 40 wt % water; more preferably 20 to 35 wt % and most preferably 22 to 30 wt % water based on the weight of the composition.

pH

The pH of preferred bars is 8 to 11, more preferably 9 to 11.

The pH of a solution is expressed as the negative logarithm of the hydrogen ion activity which is related to a millivolt potential of the pH indicating electrode. This electrode is calibrated with standard buffer mixtures whose pH values lie on either side (acidic & basic) of that of the solution which is being measured. About 1 gm of the soap bar is weighed in a beaker & made up to 100 grams by adding distilled water. This mixture is then heated to 50° C. for 10 minutes with stirring, the solution is then cooled to 25° C. and pH is measured.

The present invention provides a cleansing composition comprising: 10 to 30 wt % soap, 20 to 45 wt % water soluble organic solvent, 20 to 40 wt % water, 3 to 20 wt % electrolyte other than soap, and a benefit agent. It is preferred that total fatty matter of the composition is at most 35% by weight of the composition. It is further preferred that non-soap surfactant in the cleansing composition is up to 15% by weight of the composition.

It is preferred that the cleansing composition of the present invention includes up to 30 wt % of the benefit agent. It is most preferred that the cleansing composition of the present invention is in form of a bar. Therefore, a preferred bar of the invention may include up to 30 wt % benefit agents.

It is further preferred that the benefit agent is from 0.00005 to 5% by weight of the composition, more preferably in the range of 0.001 to 3% and most preferably 0.1 to 2.5% by weight of the composition.

It is most preferred that the benefit agent is not an antimicrobial agent.

It is preferable that the benefit agent is water insoluble and more preferable that the benefit agent is an organic compound having log P value in the range a log P value ranging from 0.4 to 12, more preferably 0.8 to 8.5 and most preferably from 1.5 to 6.5. It is most preferable that the benefit agent is present in an amount of at least 40% of saturation concentration, more preferably at least 50% and most preferably at least 55% of saturation concentration.

It is preferred that the liquid phase of the composition makes up least 65% by weight.

It is also preferred that the total fatty matter of the composition is at most 35% by weight of the composition.

It is preferred that out of the total fatty matter, surfactant is up to 15% by weight of the composition.

It is preferred that the water soluble organic solvent is a polyol.

One embodiment of the present invention provides a composition, wherein 40 to 70 wt % of the soap content is soluble soap. It is more preferable that 42 to 68 wt % of the soap content is soluble soap and most preferably, 45 to 65 wt % of the soap content is soluble soap, i.e, 40 to 70 wt % of 10 to 30% soap by weight of the composition.

In a highly preferred aspect of the present invention that the cleansing composition of the present invention is transparent.

In a preferred aspect of the present invention is provided a composition, wherein ratio of solid phase to liquid phase of the soap composition is in the range of 1:1.85 to 1:10, more preferably from 1:2 to 1:8 and most preferably from 1:2 to 1:6.

In a preferred aspect of the present invention, soluble to insoluble soap ratio ranges from 1:1.1 to 1:0.7, more preferably from 1:0.95 to 1:0.65 and most preferably from 1:0.85 to 1:0.6.

In another preferred aspect of the present invention, soap to (polyol+water) ratio is preferably in the range of 0.3:1 to 0.65:1 more preferably from 0.3:1 to 0.6:1 and most preferably from 0.2:1 to 0.5:1.

It is most preferred that the weight percentage of water and polyol in the composition is at least 50%, more preferably at least 52% and most preferably at least 55%

It is preferred that the hardness of the soap bars which is measured as edge pressing value/edge cracking value measured by the method as provided in the examples ranges from 3000 to 9500 grams, more preferably from 4000 to 8000 grams and most preferably from 6000 to 7500 grams.

Preferably, the iodine value of the soap is at most 10.

It is most preferred that the benefit agent is a fragrance.

The present invention preferably provides use of the composition for improved availability of the benefit agent. It is more preferable that the improved availability is during the intended use of the composition and most preferably, the intended use of the composition is cleansing.

The present invention preferably provides use of the composition for enhanced deposition of the benefit agent. It is more preferable that the deposition is on the surface with which the composition is contacted.

The present invention preferably provides use of 40 to 70 wt % of soluble soap of the total soap of the composition to enhance deposition of benefit agent on the skin.

The present invention preferably provides use of 40 to 70 wt % of soluble soap of the total soap of the composition to enhance fragrance boost.

The present invention provides a method of depositing a benefit agent on the surface comprising: contacting the surface with the composition of the present invention; and rinsing the surface with a suitable solvent or wiping the surface with a suitable wipe.

The present invention also provides a process for preparing the composition of the present invention, the process comprising steps of: preparing a melt of the composition at a temperature in the range of 40 to 90° C.; pouring the melt into a suitable mould; cooling the composition to a temperature in the range of 20 to 30° C.; and demoulding the composition.

Suitably the present invention can be made in the form of toilet blocks, laundry bars and the like with suitable benefit agents.

Other Preferred Ingredients

In addition to the ingredients described earlier, preferred cleansing composition may include other ingredients.

Further optional ingredients include chelating agents such as ethylene diamine tetra acetic acid, preservatives (e.g. GLYDANT®) antioxidants, and natural and synthetic perfumes. Cationic polymers may be included as conditioners. These include POLYQUATERNIUM®, MERQUAT® polymers, and JAGUAR® polymers.

The composition can also optionally include other ingredients conventionally used in soap such as lather boosters, hemectants such as, moisturisers, colourants and opacifiers.

Other adjunct materials may include germicides and preservatives. These ingredients normally will be in amounts less than 2 wt %, usually less than 0.5 wt %. Other optional ingredients like anti-oxidants, perfumes, polymers, chelating agents, colourants, deodorants, dyes, emollients, moisturizers, enzymes, foam boosters, germicides, anti-microbials, lathering agents, pearlescers, skin conditioners, stabilisers, superfatting agents, sunscreens may be added in suitable amounts in the process of the invention. Preferably, the ingredients are added after the saponification step and before filtering. Sodium metabisulphite, ethylene diamine tetra acetic acid (EDTA), borax and ethylene hydroxy diphosphonic acid (EHDP) are preferably added to the formulation.

Process

Processes for production of soaps have been described by F. W. Wells in "Soap and Chemical Specialties", Vol. XXXI, No. 6 and 7, June and July 1955.

The soap of the present invention is obtained by saponifying fatty acids or oil or their blends. Suitable fatty acids are the C8-C22 fatty acids. Fatty acids particularly suitable for the invention include stearic acid, lauric acid and palmitic acid. These can also be obtained from plant and/or animal sources, for example tallow fatty acids, palm fatty acids.

The invention will be further described by the following illustrative non-limiting examples. All parts therein are by weight % unless otherwise specified.

EXAMPLES

Control and preferred embodiments of melt cast cleansing bars were made by the usual process.

For preparing a batch size of 1 kg, 100 g palm kernel fatty acid, 200 g glycerin, 90 g stearic and palmitic acid and, 20 g castor oil and butylated hydroxyl toluene (0.1 g) were taken in a vessel and heated till the components were in a fluid state. Solution of 37% sodium citrate dehydrate was added in heated oil blend. Followed by the addition of 47% strength caustic soda lye till the mixture was completely neutralized and there was excess alkali amounting to 0.05%. After the neutralization of the mixture, 11 gm of the Perfume 1 (benefit agent) was added. 25 g additional ethanol was then added followed by addition of common salt, EDTA, EHDP, sodium lauryl sulphate, sorbitol (70 percent solution in water), sodium chloride, sorbitol and sodium metabisulphite (SMBS). The mixing was continued until a clear homogeneous mixture was obtained. Total moisture content in formula was 27% of formulation.

The soap mass was then filtered and colour and perfume were added, followed by cooling in a Schicht cooler. The cast bars were then matured under ambient conditions. After this maturation the bars were cut to a suitable size and matured for another 48 hr. The elongated bars were sliced into unit sized billets which were further stamped in stamping dies to give them distinctive rounded shape.

| | Composition of the bars | | | |
|---|---|---|---|---|
| | | | Control 1 | Control 2 |
| | | | Outside the scope of Invention | |
| Ingredients | E1 | E2 | High TFM, low electrolyte, low water | High TFM, low electrolyte, low water |
| | Inside the scope of Invention | | | |
| Soap | 25 | 25 | 76.8 | 68 |
| Sodium Lauryl Sulphate | 3 | 3 | | |
| Glycerin | 20.00 | 20.00 | 2.0 | 6.0 |
| Talc | 0 | 0 | 2.5 | 6.0 |
| Sodium Chloride | 0.80 | 0.80 | 0.8 | 0.8 |
| Sodium Citrate | 6.00 | 6.00 | 0 | 0 |
| Sorbitol | 14.00 | 14.00 | 0 | 0 |
| Water | 27.0 | 27.0 | 16 | 17 |

-continued

Composition of the bars

| Ingredients | E1 Inside the scope of Invention | E2 | Control 1 Outside the scope of Invention High TFM, low electrolyte, low water | Control 2 High TFM, low electrolyte, low water |
|---|---|---|---|---|
| Benefit agent 1* | 1.1 | 0 | 1.1 | 0 |
| Benefit agent 2** | — | 1.185 | — | 1.085 |
| Total Polyol + Water | 57.00 | 57.00 | 18.00 | 23.00 |
| Ratio of Soap to (polyol + water) | 0.44:1 | 0.44:1 | 4.32:1 | 2.95:1 |
| Other minor ingredients | upto 100 | upto 100 | upto 100 | upto 100 |

*Perfume 1 - Summer of Love 187904 HBIA (Firmenich)
**Perfume 2 - Brahmana UN 286238 GB (Firmenich)

The compositions E1 and E2 are the examples of the present invention, whereas Control 1 and Control 2 fall outside the scope of the invention for the reasons as provided in the third row of the table.

It is seen from the table that the compositions of the present invention have a low Ratio of Soap to (polyol+water) as compared to controls and total water+polyol in the preferred composition is clearly above 55% by weight of the composition.

Test Methodology

Example 1: Availability of Benefit Agent

The fragrance availability and deposition of the cleansing compositions of the present invention were evaluated across the following three consumer relevant parameters:
a) Dry sniff—as the consumer perceives the smell of the bar.
b) During Use—Fragrance from 8% soap solution indicating the bloom of the fragrance during use.
c) Post Use—Fragrance intensity—measured post rinse-off Sample Preparation:
Dry Sniff—

The consumers smell the bar to assess the fragrance of the soap, to quantify the intensity of perfume given out by the composition. To evaluate and quantify the dry sniff the fragrance in the headspace of the soap bar was measured with headspace Gas chromatography and the components were identified by mass spectroscopy. For this, samples were made by grating the soap bar with cheese grater to obtain fine particulates. 1.00 g of the composition was taken in 20 ml vial & sealed immediately with a rubber septum & equilibrated at 27° C. for 2.5 hrs to create achieve an equilibrium of the head space volatiles. Subsequently the vials were placed in an auto-sampler at 30° C.

During Use—

Consumers, evaluate the soap during use by the amount of perfume. To study the same 8% solution was made by solubilising 4 gms of grated soap in 46 gms of DM water at 50° C. in sealed vial. 3 ml of above soap solution was taken in 20 ml vial & sealed with rubber septum. Vials were equilibrated at 27° C. for 2.5 hrs & sampled similar to dry sniff samples. Subsequently the vials were placed in an auto-sampler at 30° C.

Post Use—

To quantify the deposition of the benefit agent on the skin surface. An 8% soap solution was made by procedure as described above. In vitro performance tests were performed on artificial skin samples (VITRO-SKIN™, IMS Corp., a synthetic substrate designed to mimic the surface chemistry of human skin). This 4 cm×4 cm VITRO-SKIN™ was dipped in soap solution for 15 seconds & then washed by shaking it for 30 secs in 25 ml water. The procedure is repeated for a total of 3 times with 25 ml of fresh DM water each time. The VITRO-SKIN™ was then placed in the vial & sealed immediately with a rubber septum & equilibrated at 27° C. for 2.5 hrs to create achieve an equilibrium of the head space volatiles. Subsequently the vials were placed in an auto-sampler at 30° C.

Headspace Analysis:

Samples were analyzed by gas chromatography (GC) analysis of headspace gases. In this procedure, the equipment utilized was a solid phase microextraction (SPME) system employing an Hewlett packard G1530A (GC) flame ionization detector (FID). Mass spectrometer (MS) used was Hewlett Packard 5973 mass selective detector. This equipment measured relative perfume compound abundance in the headspace over the fragrance/boosting agent/water mixture, as well as over the fragrance/water mixture. One gram of fragrance/boosting agent/water mixture was prepared in 20 ml GC headspace sampling vials sealed with caps having septums (from Gerstel, Inc.) and held at 27° C. The GC column was a DB-1 column from Agilent J&W (inner diameter 0.25 mm, length 10 m, stationary phase thickness 0.25 um). The GC conditions were as follows: Injector in split-less mode with helium gas as carrier gas. Injection port was heated to 265° C., purge flow to split vent 100 ml/min at zero minutes. Column was in constant flow mode with 0.7 ml/min flow rate. Oven temperature ramp: hold at 50° C. for 2 minutes, then increase oven temperature at a rate of 35° C./min to 100° C., 15° C./min to 200° C., 3° C./,min.

MS conditions were: solvent delay for 1 minute, scan starting from low mass 35 to high mass 300.

Autosampler's conditions were: Incubation for 30 minutes at 30° C. SPME fibre was inserted into the sample headspace for 10 minute extraction and then injected to the injector for a 1 minute desorption at 265° C.

The vials from the above three samples were analysed with capillary GC column. The PDMS (i.e. polydimethyl siloxane; apolar phase) and PEG (i.e. polyethylene glycol; polar phase) columns were used for this purpose.

The output from the GC was recorded as a series of peaks—each one representing a compound in the mixture passing through the detector. For data comparison, peak area for the peaks was obtained and added to show perfume levels. The area of a peak is proportional to amount of the compound that is present. The area can be approximated by treating the peak as a triangle. The area of a triangle is calculated by multiplying the height of the peak times its width at half height.

Table 2 shows the average sum area of peaks obtained by three different samples as described above.

TABLE 2

| Headspace results: | | | | |
|---|---|---|---|---|
| Study | E1 | Control 1 | E2 | Control 2 |
| Dry Sniff | 1913140 | 1057857 | 19486215 | 11559255 |
| During Use | 9550075 | 3195823 | 9311825 | 4382593 |
| Post Use | 259938 | 126256 | 54938.12 | 49445.11 |

The data in Table 2 shows that for the preferred cleansing compositions of the present invention, E1 and E2 as compared to Control1 and Control2, the average peak areas for E1 and E2 are much higher when compared to those of the respective Control1 and Control2 comprising the same amount of benefit agent (fragrance). Since, the area of a peak is proportional to amount of the compound that is present. It means that there is better availability of fragrance when present at same amount in the compositions of the present invention as compared to the respective Controls.

The invention claimed is:

1. A cleansing composition comprising:
 a. 10 to 30 wt. % soap,
 b. 20 to 45 wt. % water soluble organic solvent comprising a polyol,
 c. 20 to 40 wt. % water,
 d. 4 to 10 wt. % electrolyte other than soap, and
 e. benefit agent comprising a fragrance;
 wherein the soap to (polyol+water) ratio is in the range of 0.3:1 to 0.65:1; and further
 wherein the electrolyte is selected from the group consisting of sodium sulfate, sodium chloride, sodium acetate, sodium citrate, potassium chloride, potassium sulfate, sodium carbonate and other mono, di or tri alkaline earth metals salts thereof, the water and polyol collectively make up at least 50% by weight of the cleansing composition and soap in total includes at least 70 wt. % soap of $C_8$ to $C_{14}$ fatty acid.

2. A composition according to claim 1, wherein total fatty matter of the composition is at most 35% by weight of the composition.

3. A composition according to claim 1, wherein non soap surfactant is up to 15% by weight of the composition.

4. A composition according to claim 1, wherein the benefit agent is from 0.00005 to 5% by weight of the composition and the soap in total is at most 30 wt % soap of $C_{16}$ to $C_{22}$ fatty add.

5. A composition according to claim 1, wherein the benefit agent is water insoluble.

6. A composition according to claim 1, wherein the benefit agent is an organic compound having log P value in the range of 0.4 to 12.

7. A composition according to claim 1, wherein the benefit agent is present in an amount of at least 55% of saturation concentration.

8. A composition according to claim 1, wherein the water-soluble organic solvent is a polyol.

9. A composition according to claim 1, wherein 40 to 70 wt. % of the soap content is soluble soap.

10. A composition according to claim 1, wherein ratio of solid phase to liquid phase of the composition is in the range of 1:1.85 to 1:10.

11. A composition according to claim 1, wherein the benefit agent is a fragrance.

12. A method of depositing a benefit agent on a surface comprising:
 a. contacting the surface with the composition according to claim 1; and
 b. rinsing the surface with a suitable solvent or wiping the surface with a suitable wipe.

13. A process for preparing the composition according to claim 1, the process comprising steps of:
 a. preparing a melt of the composition at a temperature in the range of 40 to 90° C.;
 b. pouring the melt into a suitable mould;
 c. cooling the composition to a temperature in the range of 20 to 30° C.; and
 d. demoulding the composition.

14. A composition according to claim 1, wherein the electrolyte is selected from the group consisting of sodium sulfate, sodium chloride and sodium citrate.

15. A composition according to claim 1, wherein the soluble to insoluble soap ratio ranges from 1:0.95 to 1:0.65.

16. A cleansing composition comprising:
 a. 10 to 30 wt. % soap,
 b. 20 to 45 wt. % water soluble organic solvent comprising a polyol,
 c. 20 to 40 wt. % water,
 d. 4 to 10 wt. % electrolyte other than soap, and
 e. benefit agent comprising a fragrance;
 wherein the soap to (polyol+water) ratio is in the range of 0.3:1 to 0.65:1; further
 wherein the polyol is selected from the group consisting of glycerol, sorbitol, propylene glycol and polyethylene glycol; and
 wherein the electrolyte is selected from the group consisting of sodium sulfate, sodium chloride, sodium acetate, sodium citrate, potassium chloride, potassium sulfate, sodium carbonate and other mono, di or tri salts of alkaline earth metals thereof, the water and polyol collectively make up at least 50% by weight of the cleansing composition and soap in total includes at least 70 wt. % soap of $C_8$ to $C_{14}$ fatty acid.

17. The composition of claim 16, further comprising 2 to 10 wt. % non-soap co-surfactant.

18. The composition of claim 17, wherein the co-surfactant comprises a $C_8$ to $C_{22}$ alkyl sulphonate, sulphate ester or a mixture thereof.

* * * * *